(12) United States Patent
Moissl et al.

(10) Patent No.: US 10,406,272 B2
(45) Date of Patent: Sep. 10, 2019

(54) METHODS AND APPARATUSES FOR DETERMINING A PATIENT'S DAILY LOSS OF IRON

(71) Applicant: FRESENIUS MEDICAL CARE DEUTSCHLAND GMBH, Bad Homburg (DE)

(72) Inventors: Ulrich Moissl, Karben (DE); Volker Nier, Reichelsheim (DE); Paul Chamney, Aldbury near Tring (GB); Peter Wabel, Darmstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 458 days.

(21) Appl. No.: 15/026,319

(22) PCT Filed: Oct. 1, 2014

(86) PCT No.: PCT/EP2014/071100
§ 371 (c)(1),
(2) Date: Mar. 31, 2016

(87) PCT Pub. No.: WO2015/049320
PCT Pub. Date: Apr. 9, 2015

(65) Prior Publication Data
US 2016/0235903 A1    Aug. 18, 2016

(30) Foreign Application Priority Data
Oct. 1, 2013    (EP) ..................................... 13004747

(51) Int. Cl.
*A61M 1/34*    (2006.01)
*A61B 5/00*    (2006.01)
(Continued)

(52) U.S. Cl.
CPC ....... *A61M 1/3403* (2014.02); *A61B 5/14546* (2013.01); *A61B 5/4839* (2013.01);
(Continued)

(58) Field of Classification Search
CPC ... A61K 33/26; A61M 1/3403; A61M 1/3413; A61B 5/02042; A61B 5/0537;
(Continued)

(56) References Cited

U.S. PATENT DOCUMENTS 6,689,275 B1 * 2/2004 Gupta .................... A61K 33/26
  210/646
6,779,468 B1 * 8/2004 Gupta .................... A61K 33/26
  210/646
(Continued)

FOREIGN PATENT DOCUMENTS

WO    1992-19152 A1    11/1992
WO    2006-002685 A1    1/2006

OTHER PUBLICATIONS

Easom, Andrea. "The challenges of using serum ferritin to guide IV iron treatment practices in patients on hemodialysis with anemia." Nephrology Nursing Journal 33.5 (2006): 543.*
(Continued)

*Primary Examiner* — Adam Marcetich
(74) *Attorney, Agent, or Firm* — Fish & Richardson P.C.

(57) ABSTRACT

A method for determining or approximating a patient's daily loss of iron (fe_loss), the method comprising the steps of determining the patient's iron uptake (fe_uptake); determining the quantity of iron stored within the patient's body; and determining the patient's daily loss of iron based on the patient's iron uptake (fe_uptake) and the quantity of non-functional iron stored within the patient's body. The method relates further to apparatuses and an erythropoesis stimulating medicament for use in the treatment of anaemia. Finally
(Continued)

the present invention relates to digital storage means, a computer program product, and a computer program.

12 Claims, 9 Drawing Sheets

(51) Int. Cl.
  *A61B 5/145* (2006.01)
  *A61K 33/26* (2006.01)
  *G01N 33/90* (2006.01)
  *A61B 5/02* (2006.01)
  *A61B 5/053* (2006.01)

(52) U.S. Cl.
  CPC .......... *A61B 5/4866* (2013.01); *A61K 33/26* (2013.01); *A61M 1/3413* (2013.01); *G01N 33/90* (2013.01); *A61B 5/02042* (2013.01); *A61B 5/0537* (2013.01); *A61B 5/7246* (2013.01); *G01N 2333/805* (2013.01)

(58) Field of Classification Search
  CPC . A61B 5/14546; A61B 5/4839; A61B 5/4866; A61B 5/7246
  See application file for complete search history.

(56) References Cited

U.S. PATENT DOCUMENTS

| | | | |
|---|---|---|---|
| 2007/0012622 A1* | 1/2007 | Wash | A61K 33/00 210/647 |
| 2007/0161600 A1 | 7/2007 | Helenek et al. | |
| 2008/0015487 A1* | 1/2008 | Szamosfalvi | A61M 1/3672 604/6.07 |
| 2008/0213345 A1* | 9/2008 | Hu | A61K 9/0019 424/450 |
| 2010/0113891 A1* | 5/2010 | Barrett | A61B 5/14535 600/301 |
| 2011/0004145 A1 | 1/2011 | Beiriger et al. | |
| 2012/0016686 A1* | 1/2012 | Ryan | G06F 19/00 705/2 |
| 2012/0277655 A1* | 11/2012 | Gerber | A61B 5/0031 604/6.09 |
| 2013/0052136 A1 | 2/2013 | Chamney et al. | |
| 2013/0345303 A1* | 12/2013 | Poradosu | A61K 9/28 514/502 |
| 2014/0042092 A1* | 2/2014 | Akonur | A61M 1/16 210/646 |
| 2015/0220700 A1* | 8/2015 | Chait | G06F 19/3456 514/7.7 |
| 2015/0320920 A1* | 11/2015 | Chamney | A61B 5/0537 600/309 |
| 2016/0123998 A1* | 5/2016 | MacIntyre | A61B 5/02042 436/66 |

OTHER PUBLICATIONS

Pantopoulos, Kostas, et al. "Mechanisms of mammalian iron homeostasis." Biochemistry 51.29 (2012): 5705-5724.*
Magnussen, Karin, Nanna Bork, and Lisa Asmussen. "The effect of a standardized protocol for iron supplementation to blood donors low in hemoglobin concentration." Transfusion 48.4 (2008): 749-754.*
Newman, Bruce. "Iron depletion by whole-blood donation harms menstruating females: The current whole-blood-collection paradigm needs to be changed." Transfusion 46.10 (2006): 1667-1681.*
Ganz, Tomas. "Systemic iron homeostasis." Physiological reviews 93.4 (2013): 1721-1741.*
Hentze, Matthias W., Martina U. Muckenthaler, and Nancy C. Andrews. "Balancing acts: molecular control of mammalian iron metabolism." cell 117.3 (2004): 285-297.*
Fomon, Samuel J., et al. "Inevitable iron loss by human adolescents, with calculations of the requirement for absorbed iron." The Journal of nutrition 133.1 (2003): 167-172.*
Conrad, Marcel E., and Jay N. Umbreit. "Iron absorption and transport—an update." American journal of hematology 64.4 (2000): 287-298.*
Maher et al., Ed., "Replacement of Renal Function by Dialysis," Kluwer Academic Publisher, 5th Edition, 2004, Dordrecht, The Netherlands, (title page, copyright page, table of contents page(s) only).
International Search Report from PCT/EP2014/071100, dated Dec. 19, 2014.
Hiroshi et al. "Method for determining the amount of blood loss using the storage iron decrease rate as obtained from serum ferritin after intravenous iron therapy," US National Library of Medicine, Bethesda, MD US, Nov. 2004; and The Japanese Journal of Clinical Hematology, Nov. 2004, vol. 45, No. 11, pp. 1177-1180.
Hallberg et al., "Iron stores and haemoglobin iron de cits in menstruating women; calculations based on variations in iron requirements and bioavailability of dietary iron," European Journal of Clinical Nutrition, vol. 54, No. 8, Aug. 1, 2000, pp. 6500657.
Fomon et al., "Nutrient requirements inevitable iron loss by human adolescents, with calculations of the requirement for absorbed iron 1," The Journal of Nutrition, vol. 133, No. 1, Jan. 1, 2003, pp. 167-172.
Hunt et al., "Body iron excretion by healthy men and women," American Journal of Clinical Nutrition, vol. 89, No. 6, Apr. 22, 2009, pp. 1792-1798.

* cited by examiner

Cumulated Iron Uptake

Cumulated Iron Loss

Combined Cumulated Iron Uptake and Iron Loss

METHODS AND APPARATUSES FOR DETERMINING A PATIENT'S DAILY LOSS OF IRON

CROSS REFERENCE TO RELATED APPLICATIONS

The present application is the national stage entry of International Patent Application No. PCT/EP2014/071100, filed on Oct. 1, 2014, the disclosure of which is expressly incorporated herein by reference in its entirety, and which claims priority to Application No. EP 13004747.5, filed on Oct. 1, 2013.

FIELD OF INVENTION

The present invention relates to a method for determining a patient's daily loss of iron. It relates further to a corresponding apparatus and to medicament comprising iron for use in the treatment of anaemia. Finally, the present invention relates to a blood treatment apparatus, a digital storage means, a computer program product, and a computer program.

BACKGROUND

Management of anemia, defined as a decrease in normal number of red blood cells (RBCs) or less than the normal quantity or concentration of haemoglobin in the blood, is still a major challenge in the clinic setting. Therefore, the concentration of haemoglobin (Hb, also known as Hgb, being the iron-containing oxygen-transport metalloprotein of the red blood cells) is frequently measured by means of blood samples for assessing the anaemia state of the patient. Values below pre-set thresholds are usually considered as a sign for the manifestation of "anaemia". In case of anaemia erythropoesis stimulating agents (ESA) may be administered.

In practice, in addition or as a substitute to other erythropoesis stimulating agents iron is supplemented in order to enhance the mass or the concentration of haemoglobin. Usually, iron is supplemented based on how much the current Hb, ferritin or TSAT (transferring saturation) value differs from a target Hb, ferritin or TSAT value. Hence, the Hb, ferritin or TSAT value is regarded as an indicator of how much iron has to be supplemented.

SUMMARY

It is an object of the present invention to suggest another indicator for the amount of iron that has to be supplemented. Also, apparatuses for carrying out the method according to the invention are provided, as well as digital storage means, a computer program product, and a computer.

Accordingly, in one aspect of the invention, a method for determining or approximating a patient's loss of iron, in particular his/her daily loss of iron is proposed. The method comprises the steps a) determining, measuring or calculating the patient's iron uptake; b) determining or measuring the quantity of iron stored within the patient's body; and c) determining or calculating the patient's daily loss of iron based on the patient's iron uptake and the quantity of iron, in particular non-functional iron, stored within the patient's body.

In another aspect of the invention, an apparatus configured for determining or approximating a patient's daily loss of iron is proposed. The apparatus comprises a device configured for inputting information about the patient's iron uptake; a device configured for determining a or the quantity of iron stored within the patient's body; and a device configured for determining the patient's daily loss of iron based on the patient's iron uptake and the or a quantity of iron stored within the patient's body.

In another aspect of the invention, a blood treatment apparatus is proposed that comprises at least one apparatus for determining the daily iron loss according to the present invention or is in signal communication therewith. The apparatus also comprises a device for administering a medicament to a patient. The medicament is iron or comprises iron. The device for administering the medicament is in signal communication with the apparatus for determining the daily iron loss.

According to yet another aspect to the invention, a medicament comprising or consisting of iron for use in the treatment or prevention of anaemia or for enhancing haemoglobin concentration in a patient's blood is suggested. It features that the dose of iron or the medicament to be administered is set to substitute or to equal the amount of iron determined to have been lost since the last iron substitution based on the daily loss determined by the method according to the present invention.

The patient can be either a human being or an animal. The patient may be sound or ill. The patient may be in need of medical care or not.

In another aspect of the invention, a digital storage means, in particular a disc, CD, or DVD, has electrically readable control signals which are able to interact with a programmable computer system such that a method according to the invention will be executed.

A digital, particularly a non-volatile, storage medium according to the present invention, (also termed here as a carrier), particularly in the form of a diskette, RAM, ROM, CD, hard disk, DVD, USB stick, flashcard, SD card or EPROM, particularly with electrically or optically readable control signals, can interact with a computer or computer system in such a way that the steps of a method according to the invention, as described herein, can be prompted in cooperation with the required devices or hardware.

Thereby all, some, or a few of the implemented steps of the method according to the invention can be prompted.

In another aspect of the invention, a computer program product has a program code stored on a machine readable data medium for executing a method according to the invention when executing the program product on a computer.

A computer program product according to the present invention features a volatile, non-permanent, or a machine readable carrier or program code, saved on a storage medium, for prompting the steps of the method according to the present invention in cooperation with the required devices or hardware when the computer program product runs on a computer. A computer program product can, according to the present invention, be understood as, for example a computer program saved on a carrier, an embedded system as a comprehensive system with a computer program (e.g., an electronic appliance with a computer program), a network of computer implemented computer programs (e.g., a client-server system, Cloud computing system, etc.), or a computer on which a computer program is loaded, run, saved, implemented or developed.

A machine readable carrier designates in certain embodiments of the present invention a carrier with contains software and/or hardware interpretable data. The carrier can be a floppy disk, a CD, DVD, a USB stick, a flashcard, an SD card and the like.

In another aspect of the invention, a computer program has a program code for the execution of a method according to the invention when executing the program on a computer.

A computer program according to the present invention includes a program code for prompting the steps of the method according to the present invention when the computer program runs on a computer, in cooperation with the required devices or hardware. According to the present invention a computer program can be understood as, for example, a physical software product which is ready for use and features a program.

It holds also true for the computer program product and the computer program according to the present invention that all, a few or some of the implemented steps of the method according to the present invention can be implemented.

In all of the following exemplary embodiments, the use of the expression "may be" or "may have" and so on, is to be understood synonymously with "preferably is" or "preferably has", respectively, and so on, and is intended to illustrate exemplary embodiments according to the present invention. Also, 'configured' may be understood as 'programmed' in some embodiments according to the present invention.

Embodiments according to the present invention can include one or more of the following features in arbitrary combinations.

In certain embodiments according to the present invention, the method is a computer-implented method.

In some embodiments according to the present invention, some or all steps of the method are carried out by one or more devices provided and/or programmed for carrying out the respective step(s). One of these devices may be a device capable of performing measurement, e. g., the patient's iron uptake and/or the quantity of iron stored within the patient's body, and/or calculating, e. g., the patient's daily loss of iron.

In certain embodiments according to the present invention, the 'determining' means 'measuring'.

In some embodiments according to the present invention, the 'determining' means 'calculating'.

In certain embodiments according to the present invention, the programmable computer is or comprises a device capable of performing measurements.

In some embodiments according to the present invention, the quantity of iron stored within the patient's body is calculated by adding at least a value representing the functional iron comprised by the patient and a value representing the quantity of non-functional iron stored within the patient's body, wherein non-functional iron is defined as iron that is not contained in oxygen-transport metalloproteins.

In certain embodiments according to the present invention, for determining the functional iron comprised by the patient at least one of the haemoglobin value (Hb) and the blood volume or the absolute amount of Hb is used (or considered or taken into account in other embodiments according to the present invention); and/or for determining the quantity of non-functional iron stored within the patient's body in any tissue but the red blood cells or Hb the concentration of ferritin found in blood serum is used.

In some embodiments according to the present invention, for determining the patient's iron uptake the patient's uptake (iv-uptake (i.e., intravenous uptake, short: i.v.-uptake) or total uptake) is cumulated over time (e.g., since the last iron substitution or also longer). Also, a ferritin curve indicating the development of the ferritin concentration (gained from ferritin measurements) over time is optionally determined.

In certain embodiments according to the present invention, the method comprises calculating (or approximating) the patient's daily loss of iron using the formula:

$$fe\_loss = fe\_stored - fe\_uptake \quad (1)$$

with:
fe_loss the patient's loss of iron
fe_stored the quantity of iron stored within the patient's body
fe_uptake the patient's iron uptake In certain embodiments according to the present invention, the quantity of iron stored within the patient's body—or fe_stored—is the sum of the functional plus the non-functional iron. In other embodiments, the quantity of iron stored within the patient's body is the non-functional iron.

In some embodiments according to the present invention the quantity of iron stored is a change of iron stored or a derivative with respect to time or time derivative thereof. The same may apply in certain embodiments to the non-functional iron and/or the functional iron.

In some embodiments according to the present invention both the loss patient's up-take of iron and the loss of iron may be considered starting from one point of time (one particular day, the day of the last iron supplement or administration, and the like).

In certain embodiments according to the present invention the loss or iron is related to the day as time span. It may, however, state the loss that happens within 48 hours, and so on. This is still covered by the present invention since such loss can easily be related to the time span of one day (24 hours).

In some embodiments according to the present invention, the method comprises calculating (or approximating) the patient's daily loss of iron using the formula:

$$fe\_loss = fe\_non\text{-}functional\_stored + fe\_Hb - fe\_uptake \quad (2)$$

with:
fe_loss the patient's loss of iron
fe_non-functional_stored the quantity of iron stored within the patient's body outside of Hb
fe_Hb the quantity of iron stored within the haemoglobin (Hb)
fe_uptake the patient's iron uptake In certain embodiments of the present invention, the method comprises measuring at least one of haemoglobin value (Hb), blood volume and concentration of ferritin in serum.

According to some exemplary embodiments according to the present invention, the method for determining or approximating a patient's daily loss of iron comprises the steps:

determining the patient's iron uptake (fe_uptake);
determining the quantity of iron stored within the patient's body; and
determining the patient's daily loss of iron based on the patient's iron uptake (fe_uptake) and the quantity of functional or non-functional iron, or both, stored within the patient's body;
counting or cumulating the amount of iron administered to the patient over a set period of time;
measuring, during the set period of time, at several times values for functional iron, e.g., the Hb concentration in blood, and non-functional iron, e.g., the ferreting concentration in blood, or stored iron, in particular at times (or every time) when iron was administered;

choosing or assuming, in particular in a preliminary manner, a constant value for the average daily iron loss, e.g., 4 mg/day, for the loss during the set period of time;

calculating a value representing the relation between the iron balance (the balance being represented, e.g., by a curve representing the sum of the patient's iron uptake, the patient's iron loss, and the functional iron on several occasions within the set period of time, or as a formula, e.g., as fe_uptake+fe_loss–fe_Hb, which may be called the 'fe_estimated_stored'-curve or formula) and a non-functional iron curve over time for the set period of time (the value representing the relation being, for example, a correlation marker, e.g., a correlation coefficient or any other measurement for measuring a statistic relationship);

comparing the calculated relation with the relation(s) gained for at least one other iron balance based on another average daily iron loss (for example 3 mg/day or 5 mg/day but the same values of the patient's iron uptake, the patient's iron loss, and the functional iron) or with a pre-set threshold or pre-set criterion;

selecting one of the assumed average daily iron losses as dose for iron to be replaced or administered.

According to certain exemplary embodiments according to the present invention, the steps:

determining the patient's iron uptake (fe_uptake);

determining the quantity of iron stored within the patient's body; and determining the patient's daily loss of iron based on the patient's iron uptake (fe_uptake) and the quantity of functional or non-functional iron, or both, stored within the patient's body;

are carried out or embodied by counting or cumulating the amount of iron administered to the patient over a set period of time;

measuring, over the set period of time, at several times values for functional iron, e.g., the Hb concentration in blood, and non-functional iron, e.g., the ferreting concentration in blood, or stored iron, in particular at times (or every time) when iron was administered;

choosing or assuming a constant value for the average daily iron loss, e.g., 4 mg/day, for the loss during the set period of time;

calculating a value representing the relation between the iron balance (e.g., a curve representing the sum of the patient's iron uptake, the patient's iron loss, and the functional iron (e.g., Hb) on several occasions within the set period of time, e.g., as fe_uptake+fe_loss–fe_Hb, which may be called the 'fe_estimated_stored'-curve) and a non-functional iron curve (e.g., ferritin) over time for the set period of time (such as a correlation marker, e.g., a correlation coefficient or any other measurement for measuring a statistic relationship);

comparing the calculated relation with the relation(s) gained for at least another iron balance based on another average daily iron loss (but the same values of the patient's iron uptake, the patient's iron loss, and the functional iron) or with a pre-set threshold or criterion;

selecting one of the assumed average daily iron losses as dose for iron to be replaced or administered.

In some embodiments, the apparatus according to the present invention comprises a device configured for calculating the quantity of iron stored within the patient's body by adding at least a value representing the functional iron comprised by the patient and a value representing the quantity of non-functional iron stored within the patient's body.

In certain embodiments according to the present invention, the apparatus comprises a device configured for determining the functional iron comprised by the patient by determining at least one of haemoglobin value (Hb) and blood volume and/or a device configured for determining the quantity of non-functional iron stored within the patient's body by determining the concentration of ferritin in serum.

In some embodiments according to the present invention, the apparatus comprises a device configured for determining the patient's iron uptake, wherein the patient's uptake is cumulated over time; and a device configured for determining a ferritin curve indicating the development of ferritin measurements over time.

In certain embodiments according to the present invention, the apparatus comprises a device configured for calculating (or approximating) the patient's daily loss of iron using the above stated formulae (1) or (2).

In some embodiments according to the present invention, the apparatus comprises a device configured for measuring at least one of haemoglobin value (Hb), blood volume and concentration of ferritin in serum.

In certain embodiments according to the present invention, the blood treatment apparatus is configured as a dialysis machine, a hemodiafiltration apparatus, or a hemofiltration apparatus.

In certain embodiments according to the present invention, the blood treatment apparatus is a device for administering a medicament, such as apparatuses available on the market under the trademarks "perfusor" or "infusomat" and/or a device disclosed in US 20110004145 A1, the disclosure of which is hereby explicitly incorporated in the present application by reference.

In some embodiments according to the present invention, the term "based on" means "taking into account", "considered in a mathematical approximation or calculation", or the like. In certain embodiments according to the present invention, the terms "calculation" and "approximation" may be substituted or interchanged by each other.

In particular embodiments according to the present invention, a constant iron loss is assumed. In some embodiments, at least three different constant values are assumed (or estimated) for the iron loss. In certain embodiments of the present invention, between four and ten of such different, constant iron losses are assumed. For each of the assumed iron loss value, a curve is determined that reflects changes in the concentration of the stored iron. The curve may be drawn or determined based on at least two values belonging to the group that consists of the cumulated iron uptake, the assumed constant iron loss and the functional iron stored within the patient's body. In some embodiments according to the present invention, a statistic relation is determined by relating the ferritin curve of the patient to the curve that reflects the change of iron stored in the patient's body. In these embodiments, the value of the assumed constant daily iron loss that fits best with regards to statistic correlation is determined or set as the actual daily iron loss, representing the result achieved by the present method.

In some embodiments of the present invention, the ferritin value is the ferritin concentration of the patient's blood serum.

In certain embodiments according to the present invention, upon starting the method according to the present invention, or as a start value thereof, the daily loss or the required iron substitute is assumed to be between −5 mg/day and 20 mg/day. Values comprised by this range are tested for the magnitude of their correlation.

In some embodiments according to the present invention, the iron substitution actually needed by the patient is set as a value being equivalent or identical to the amount of iron determined as the daily loss.

In some embodiments according to the present invention, the patient in question suffers from impaired renal function or cancer and/or requires dialysis.

In some embodiments according to the present invention, determining the dose or any other value means approximating or calculating it.

In certain embodiments according to the present invention, the concentration or the mass of haemoglobin is directly measured, e.g., from blood samples or by means of optical methods, e.g., without having drawn blood from a vessel as it is known in the art. In addition, or alternatively, the values at issue may be derived from other values, parameters, etc., which allow a correct calculation or at least a sufficient approximation of haemoglobin (Hb), its concentration or the haemoglobin (Hb) state.

In certain embodiments, the blood volume (V_blood) is approximated, calculated or defined based on measured values and/or calculations based on measurements made by a body composition monitor. Regarding its features it is referred to WO 2006/002685 A1. The respective disclosure of WO 2006/002685 A1 is hereby incorporated by way of reference. It is to be understood that the blood volume can be determined in different ways, all of which are known to the person skilled in the art.

In certain embodiments, a target or a target range is defined by means of one threshold or a combination of more than one threshold.

Of course, the monitor used for determining the blood volume must not be understood to be limited to monitors measuring the bioimpedance or to monitors as described in WO 2006/002685 A1. Monitors based on other methods known in the art such as dilution measurements, anthropometric equation(s) and also any other method known to the skilled person are also contemplated and encompassed by the present invention as well.

In certain embodiments, the apparatus comprises a monitor for measuring Hb concentrations (e.g., in [g/dl]) and/or for determining the blood volume by means of any monitor as described in "*Replacement of Renal Function by Dialysis*" by Drukker, Parson and Maher, Kluwer Academic Publisher, $5^{th}$ edition, 2004, Dordrecht, The Netherlands, on pages 397 to 401 ("*Hemodialysis machines and monitors*"), the respective disclosure of which is hereby incorporated by way of reference.

In some embodiments, the monitor is configured to measure the blood volume and/or the concentration of Hb by means of measuring an electrical conductivity.

In certain embodiments, the monitor is configured to measure the blood volume and/or the concentration of the Hb by means of measuring an optical density.

In some embodiments, the monitor is configured to measure the blood volume and/or the concentration of Hb by means of measuring a viscosity.

In certain embodiments, the monitor is configured to measure the blood volume and/or the concentration of the Hb by means of measuring a density.

In some embodiments, the monitor comprises one or more corresponding probes and/or one or more sensors for carrying out the measurements such as electrical conductivity sensors, optical sensors, viscosity sensors, density sensors, and the like.

In another aspect, the present invention relates to a method for monitoring iron stored by the patient. This method requires that a dosage of iron was set before starting the present method. This dosage is being assumed to have been administered to the patient in the past on a regular basis no matter whether iron has actually been administered or not. The method now comprises the following steps. First, a first monitoring time and a second monitoring time are being set, defining the start time and the end time of a time window for monitoring. Second, an upper and a lower threshold for the haemoglobin value, the ferritin value, or both, is set. Third, within the time window the haemoglobin value, the ferritin value, or both, are being monitored to be within or between the set thresholds. In certain of these embodiments, the width of the time window is set to encompass at least two points of time when two haemoglobin values of the patient or two ferritin values, or both, have been measured. The width is set such that it encompass also the time of at least one dosage of iron administered to the patient. In certain embodiments of this method it also encompasses the step of determining a first constant iron loss of the patient for which a first, best statistic relation can be established between curves or values found within the set time window. This step may be carried out as described anywhere herein. In these embodiments, the time window may be spread until either the first, best statistic relation's probability of error falls below a pre-set threshold for the statistical error (e.g., by the method of least squares), or until the time window has been spread up to a pre-set maximum width. In certain embodiments according to the present invention, the width of the time window may be constant or variable (e.g., by setting its begin and its end). In some embodiments according to the present invention, the time window may be moved along the time axis.

In some embodiments of this method, the method encompasses the step of comparing the first constant iron loss with a pre-set or pre-determined second constant iron loss of the patient based on which the dosage of iron administered to the patient on a regular basis was (actually or virtually) set before starting the present method. An alarm is triggered if at least one of the following features or conditions is met: a) the difference or numerical difference between the first constant iron loss and the second iron loss exceeds a pre-set iron loss threshold; b) the difference between the probability of error of the first constant iron loss and the probability of error of the second constant iron loss exceeds a pre-set threshold; c) the difference between the best statistic relation belonging to the first constant iron loss and the best statistic relation belonging to the second constant iron loss exceeds a pre-set threshold; and d) the real or de facto correlation falls below a pre-determined correlation threshold being or representing the best fitting correlation.

In certain embodiments, the apparatus is configured also for treating a patient by means of dialysis.

In other embodiments, the apparatus is configured for treating a patient (or the patient's blood) by hemofiltration, ultrafiltration, haemodialysis, etc.

The present invention may in certain embodiments provide for one, some or all of the advantages stated herein.

For example, knowing the daily loss of iron may allow for providing a more precise supplement of iron. Also, it may allow for supplementing iron in smaller but more frequent dosages.

Knowing the daily loss which may in turn lead to a more frequent administration of iron and to an alternative to the state of the art administration of iron in which iron is only administered if certain anaemia parameters such as Hb are found to be outside of target boundaries. This well-known on-off dosage scheme often results in Hb cycling around the threshold without ever being properly adjusted. The present invention provides the information needed to counteract the Hb cycling.

According to some embodiments of the present invention, a shift of iron between various compartments such that, e.g., the concentration of non-functional iron declines whereas the concentration of functional iron rises, or vice versa, while these changes are not due to loss or uptake of iron, can also be considered. This advantageously contributes to enhancing the preciseness with which the loss is calculated.

Also, the present invention advantageously provides devices and methods for achieving the advantages described herein.

Other aspects, features, and advantages will be apparent from the description, figures, and claims. However, the invention must not be understood to be limited to this example. Identical reference numerals used in the figures depict identical or similar elements.

DETAILED DESCRIPTION

According to one exemplary embodiment according to the present invention, it is proposed that ferritin may be used as a marker related to iron stores, in particular to non-functional iron stores. Its concentration over time may be linear (alternatively also non-linear, but defined by a mathematical function) to the iron stores. According to this embodiment, a model is proposed, incorporating iron stored in a first compartment (liver, bone marrow, spleen), a second compartment (iron stored in Hb). Optionally, a third compartment covering iron comprised in muscle is comprised as well. Over a certain period of time, the amount of iron administered to the patient is recorded, together with values for Hb and ferritin. Then a constant value for the average daily iron loss is chosen or estimated, and a value representing the relation between the iron balance (uptake vs. losses and internal shifts between Hb and stores) and ferritin is determined. This procedure is repeated a number of times over a certain range of assumed constant daily iron losses, and the loss which gives the highest correlation marker (e.g., a correlation coefficient or any other measurement for measuring a statistic relationship) is selected as the determined average daily iron loss. The such determined average daily iron loss may then be replaced by intravenously ("iv") administered iron in a step subsequent to the method of the present invention. The afore-mentioned exemplary embodiment is further described with respect to the figures.

Figure 1A:
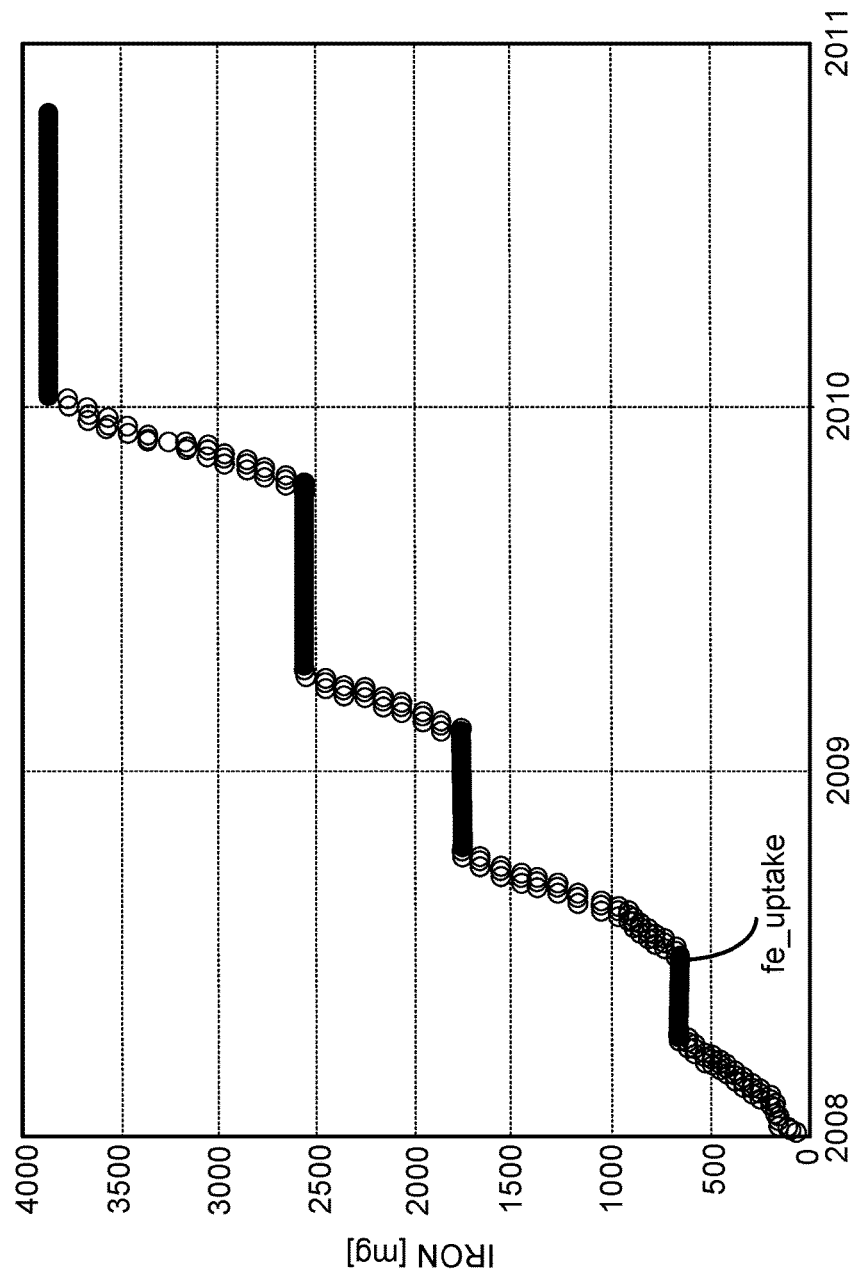
FIG. 1a shows a curve of a cumulated intravenous (short: "iv") iron uptake of a patient.

FIG. 1a shows a curve of a cumulated (iv) iron uptake fe_uptake over time of a patient in a iron concentration (in [mg]) over the time [year] diagram (these dimension have also been chosen for the FIGS. 1b, 1c, 2, 3 and 6 at the top). The inclinations of some of the curve's sections are due to iv iron administrations, administered in or at constant time intervals.

Figure 1B:
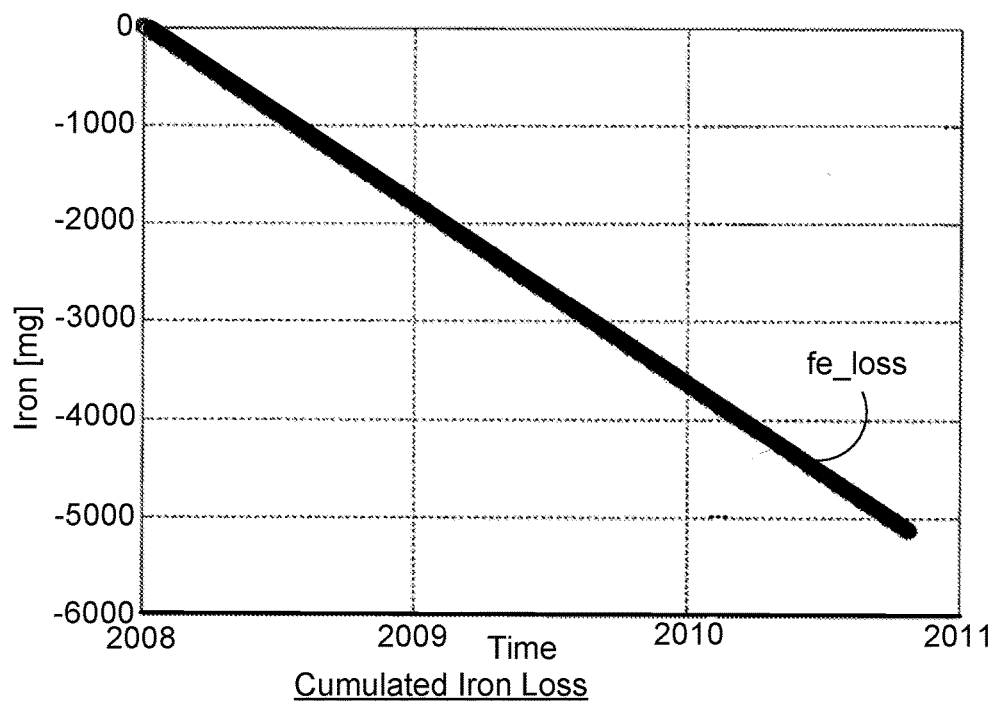
FIG. 1b shows a curve of a cumulated daily iron loss of the patient.

FIG. 1b shows a—e. g. estimated—curve of a cumulated—e. g. assumed—daily iron loss fe_loss of the patient. A linear curve is assumed since an individual but yet constant daily iron loss is assumed. Iron is mostly lost by bleeding or due to the dialyser's effect on the erythrocytes.

Figure 1C:
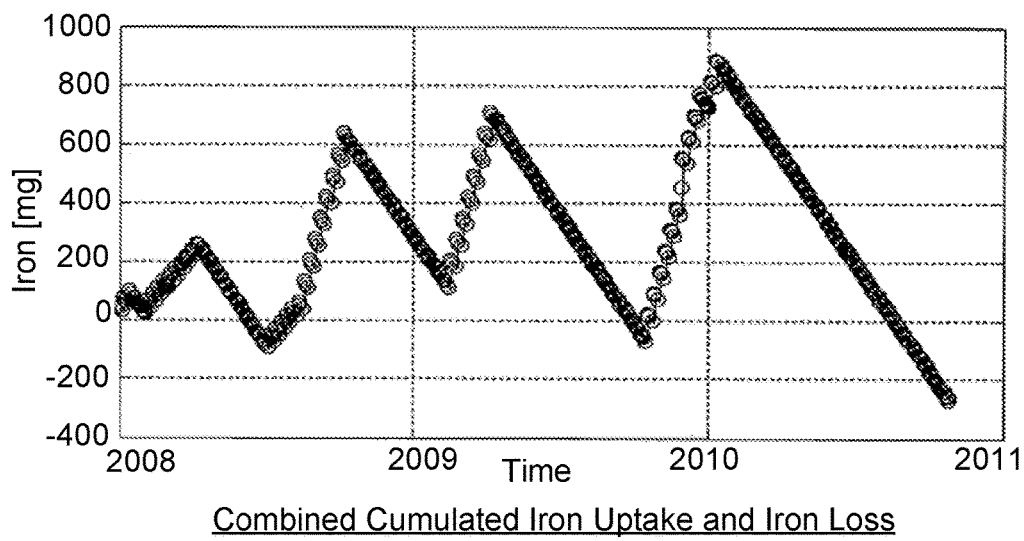
FIG. 1c shows a curve of a combined cumulated iv iron uptake and daily loss of the patient.

FIG. 1c shows a curve of a combined cumulated (iv) iron uptake and daily loss of the patient.

In the curves of the preceding figures, inflammation, blood transfusions and changes in dialyzers etc. are neglected. If these were to be considered, the curves would have to be adapted as is also encompassed by the present invention.

Figure 2:
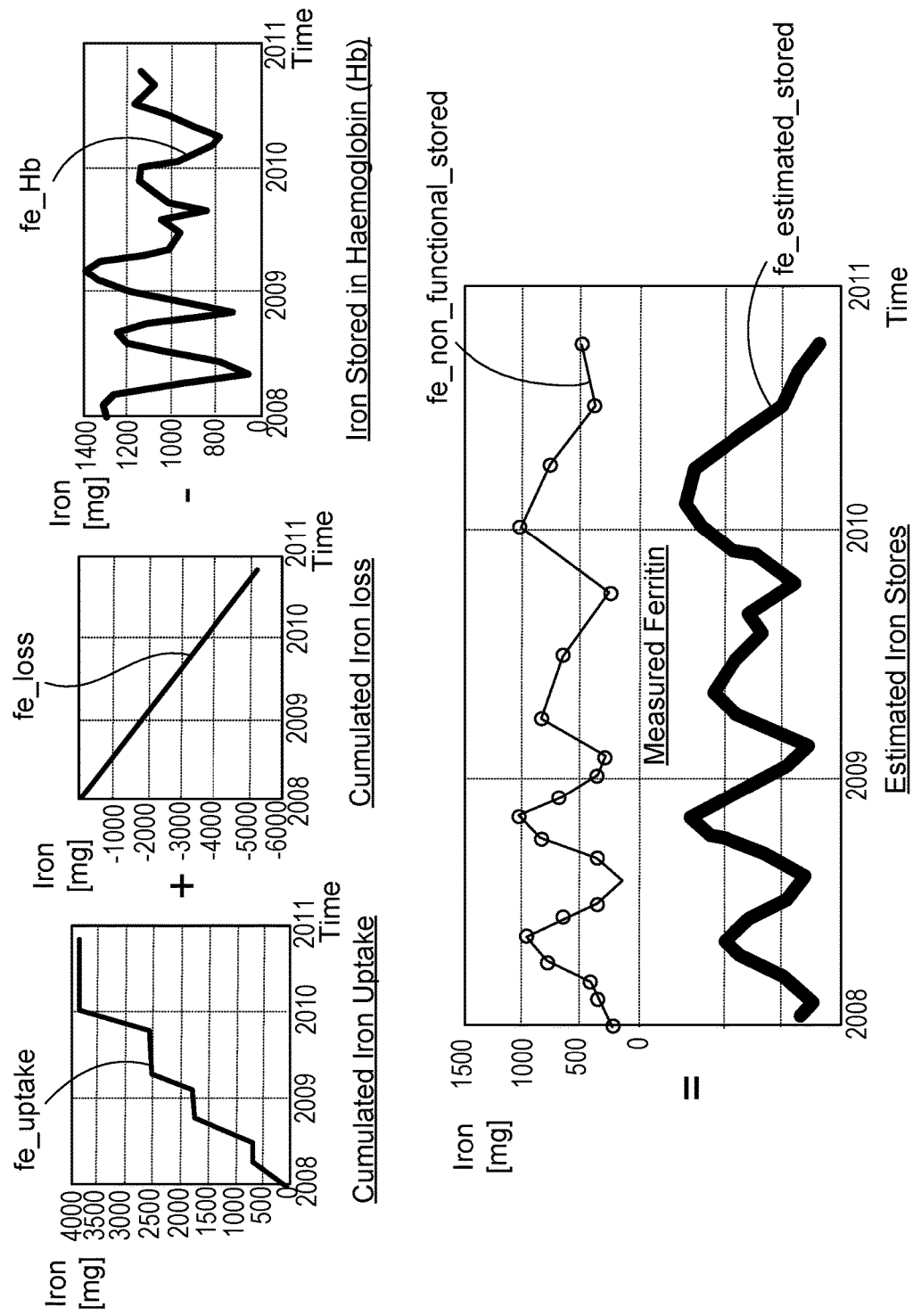
FIG. 2 reflects the above discussed formulae.

FIG. 2 reflects the above discussed formulae. The illustration at the bottom shows in its upper part the development of ferritin as a marker of the non-functional iron store, indicated as fe_non-functional_stored. The ferritin values may be measured. In its lower part the illustration shows the estimated iron stores, depicted as fe_estimated_stored. The latter value may be gained by fe_uptake+fe_loss−fe_Hb as indicated by FIG. 2 (see the three diagrams at the top of FIG. 2).

FIG. 2 shows that the ferritin curve has a shape similar to the development of the estimated iron stores over time. Hence, the assumed loss fe_loss illustrated in FIG. 2 (see the middle diagram at the top) which influences the shape of curve fe_estimated_stored quite strongly and which is the only value that has not been measured but estimated in the example of FIG. 2 has been selected quite thoroughly.

Figure 3:
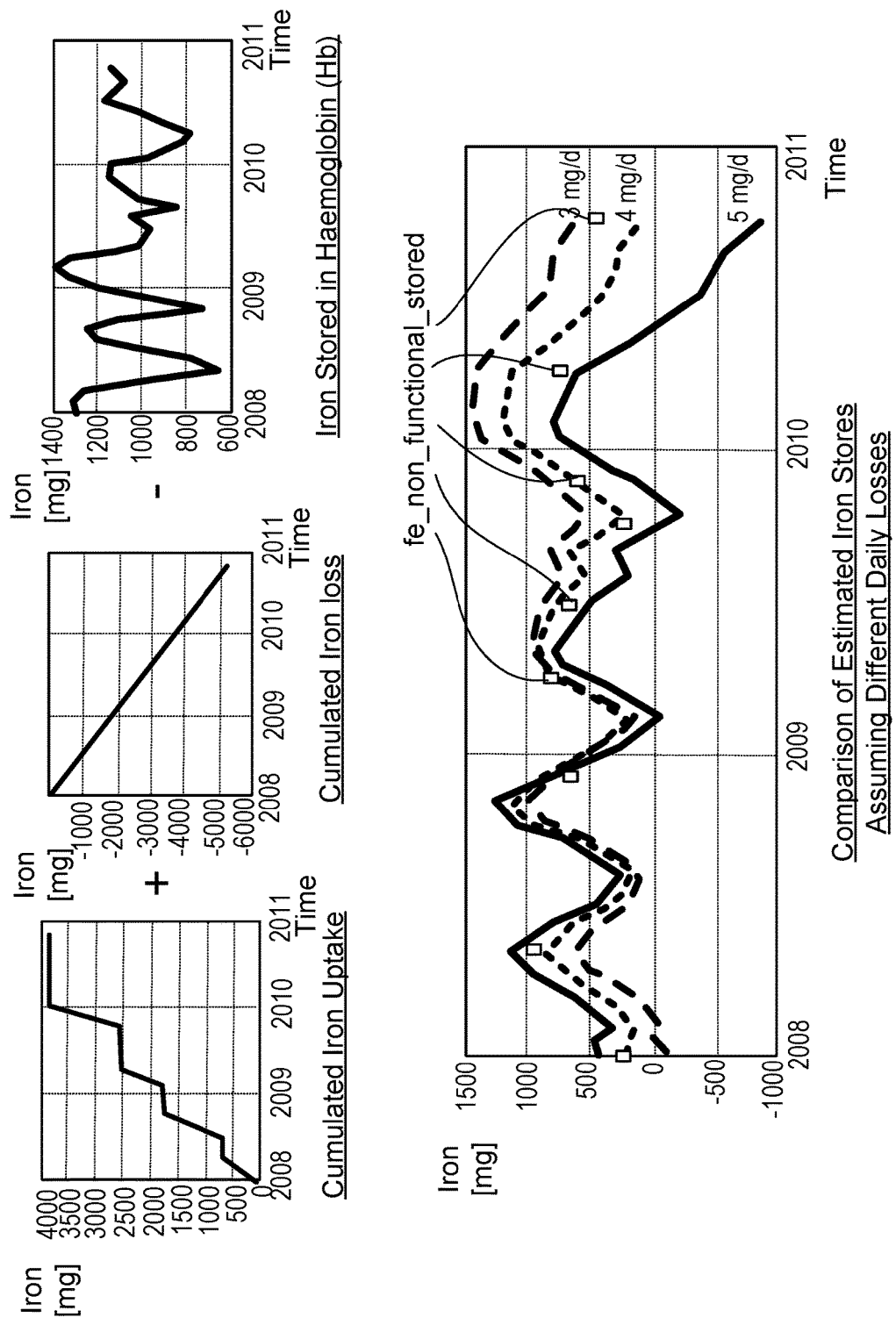
FIG. 3 shows a comparison of different daily iron losses.

FIG. 3 shows a comparison of different daily assumed iron losses. In FIG. 3, the curve fe_non-functional_stored is only indicated by dots representing the ferritin values measured at different points of time.

As can be seen from FIG. 3, assuming the daily loss as 4 mg/day results in a loss curve that follows the (not fully drawn) ferritin curve fe_non-functional_stored more precisely than the curves that correspond to 3 mg/day and 5 mg/day, respectively. Hence, the daily loss may be considered to be closer to 4 mg/day than to 3 mg/day or to 5 mg/day.

Figure 4:
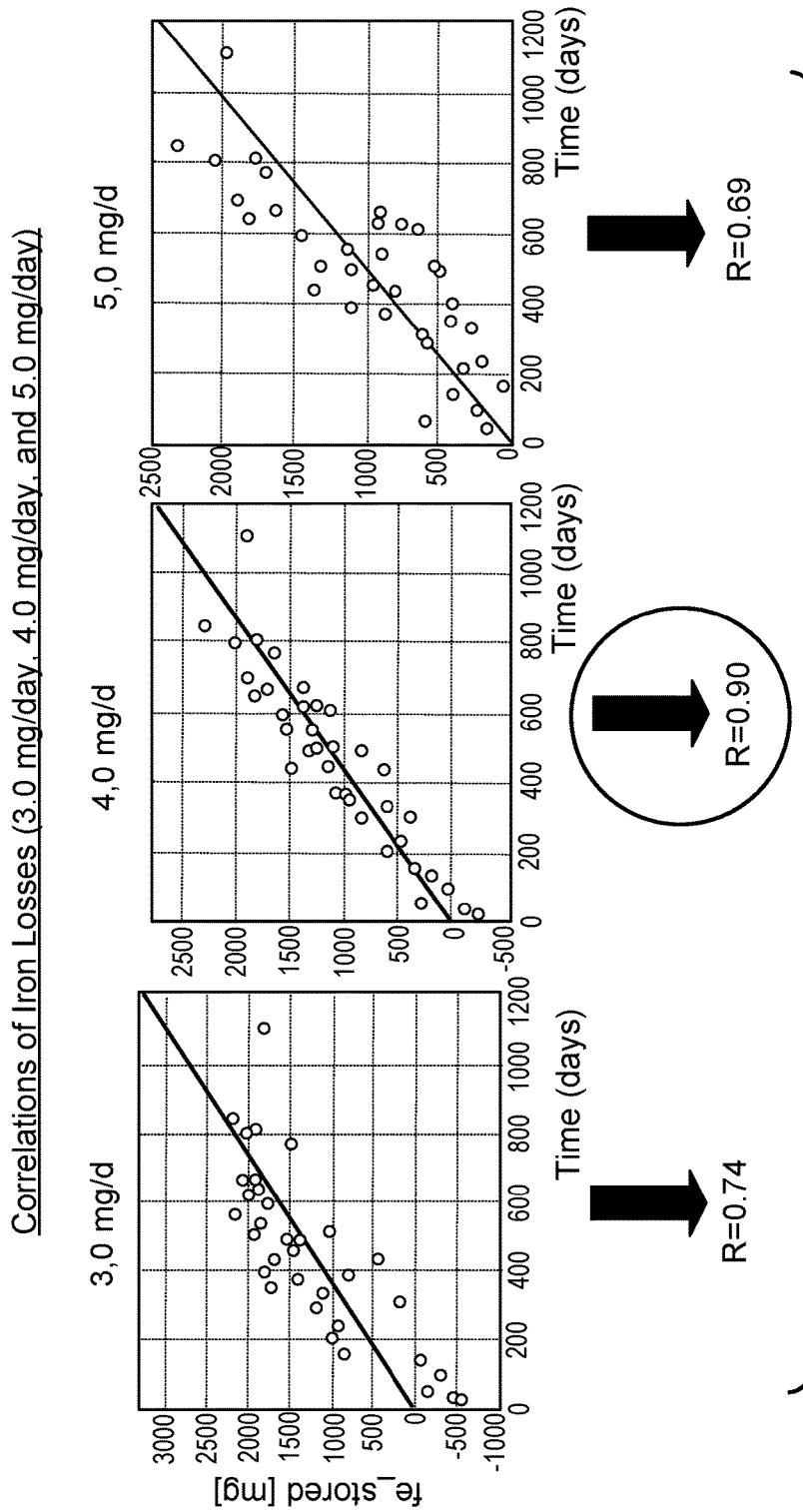
FIG. 4 shows the respective correlation of three different iron losses.

FIG. 4 shows the respective correlation of three different iron losses of 3.0 mg/d, 4.0 mg/d and 5.0 mg/d, respectively, in a diagram showing the stored iron fe_stored in [mg] over ferritin in [ng/ml].

As can be seen in the example of FIG. 4, the assumed loss of 4.0 mg/d has the best correlation (expressed by the correlation coefficient R) of all three losses.

Figure 5:
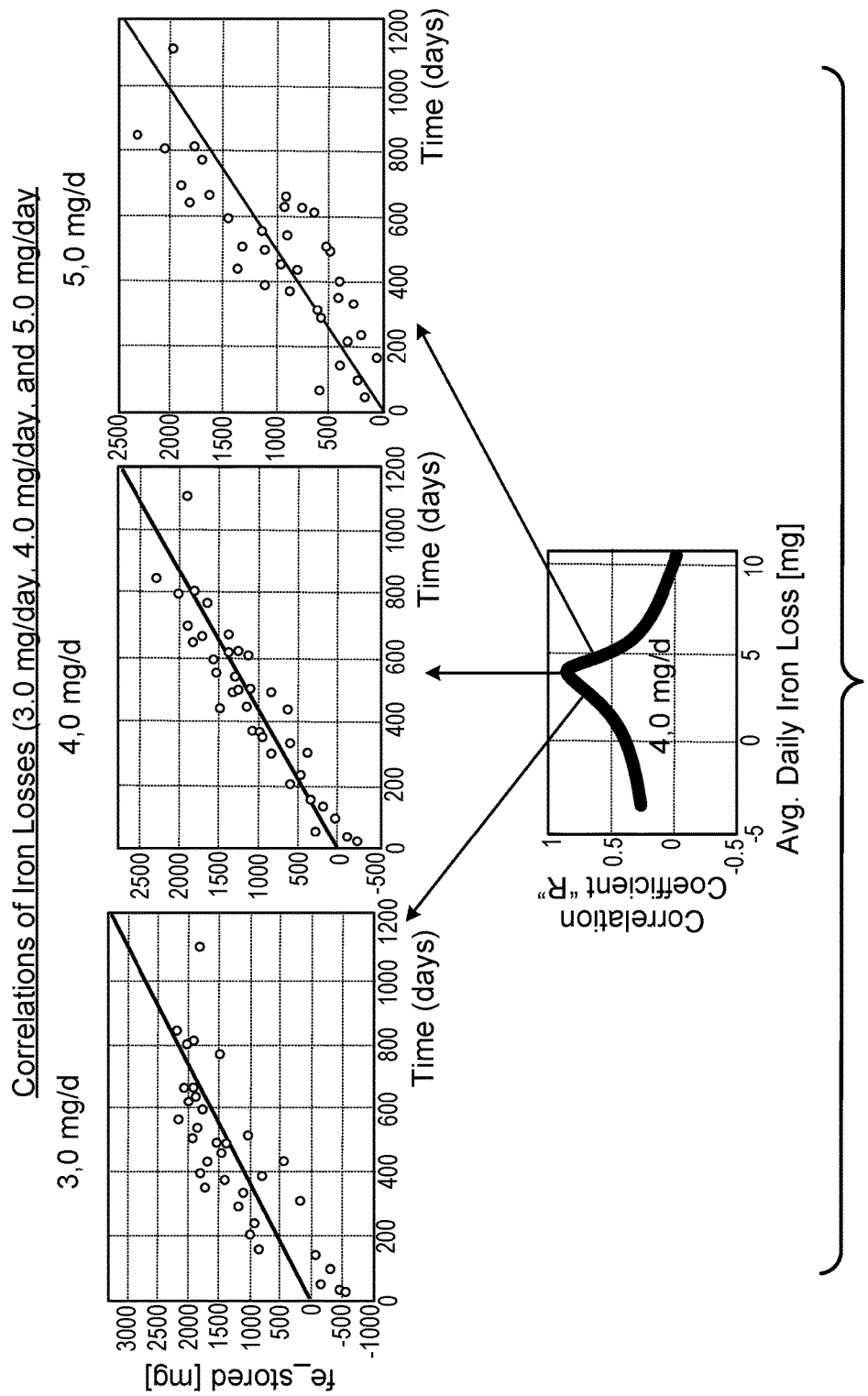
FIG. 5 shows the findings of FIG. 4 in another illustration.

FIG. 5 shows the findings of FIG. 4 in another representation. As can be seen from the diagram at the bottom of FIG. 5, in a correlation-coefficient-R over average-daily-iron-loss [mg]-plot the highest correlation coefficient R is found for 4.0 mg/d.

Figure 6:
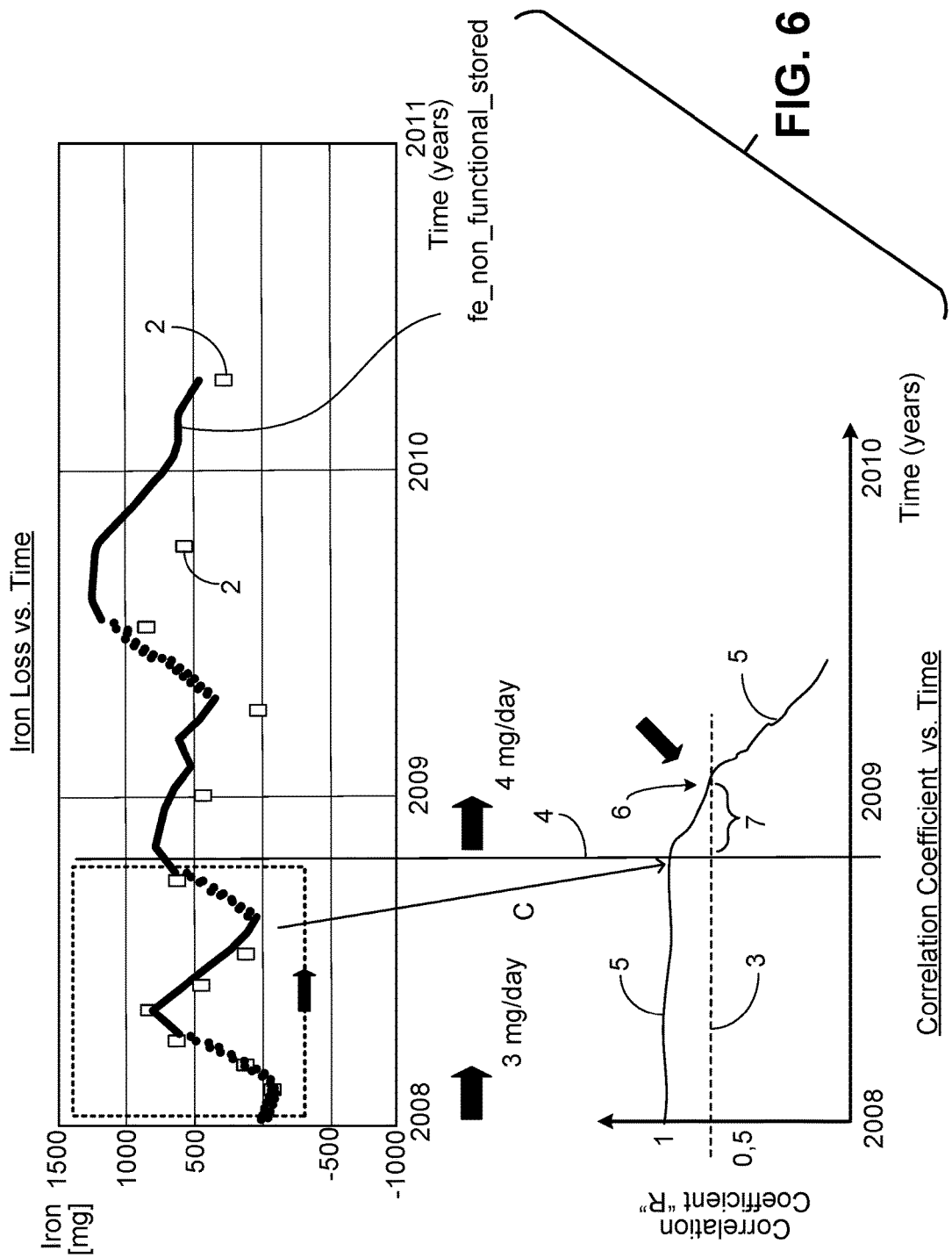
FIG. 6 shows the findings of FIG. 4 in another illustration.

FIG. 6 shows a sliding window 1 (see the dotted lines) used for calculating the correlation and/or for detecting changes in daily iron loss. The rectangular measurements 2 reflect the measured ferritin values gained at the day of testing. The line 'fe_non_functional_stored' represents the curve of or at an estimated iron loss of 3 mg/day.

As is indicated by the short arrow attached to the sliding window 1, the window 1 moves along the time axis over or with time.

As is indicated by the long arrow 'C' interconnecting the diagram at the top of FIG. 6 with that at the bottom thereof, the correlation is calculated for each position of the sliding window 1 over the time axis. The result is checked or even plotted against a pre-determined correlation threshold 3 (see the lower diagram in FIG. 6 illustrating the correlation over time). The pre-determined correlation threshold 3 may be or represent the best fitting correlation gained by the method described with respect to FIGS. 3 to 5. However, the predetermined correlation threshold 3 may also be determined another way or simply set.

The vertical line 4 marks the day when the up to that point true loss of 3 mg/day turns into a loss of 4 mg/day. As can be seen in FIG. 6, the change in daily loss that takes place at the vertical line 4 is only detected when the correlation threshold 3 is crossed by the correlation curve 5 at a crossing point 6. Because of the nature of sliding windows, there is a time delay between the day when the true iron loss changes due to whatever reason and the day when the change is detected. In the example of FIG. 6, this time delay corresponds to the difference between the vertical line 4 and the crossing point 6. It is marked by the reference numeral 7.

Figure 7:
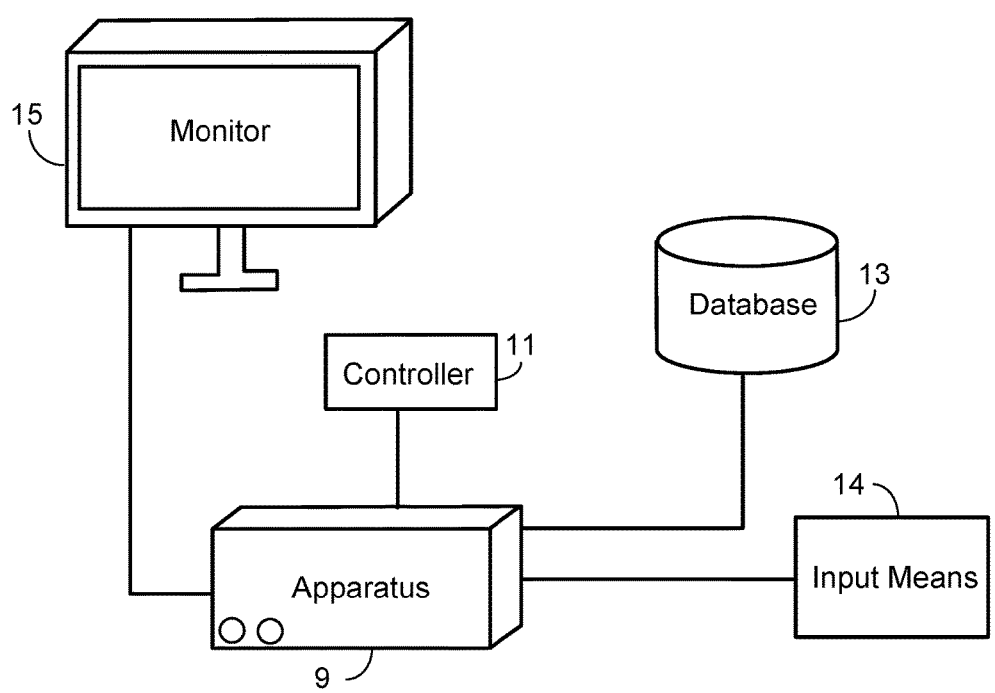
FIG. 7 shows a first apparatus according to the present invention comprising a controller for carrying out the method according to the invention.

FIG. 7 shows an apparatus 9 comprising a controller 11 for carrying out the method according to the invention. The apparatus 9 is connected to an external database 13 comprising the results of measurements and all other data needed for the method according to the invention. The database 13 can also be an internal means. The apparatus 9 may optionally have means 14 for inputting data into the controller 11 or into the apparatus 9. Such data may be information about the functional iron store such as the mass, the volume, the concentration of Hb and/or information about the non-functional iron store such as ferritin as is set forth above. Such data input into the apparatus 9 may—additionally or instead of—also comprise information about the blood volume of the patient or an approximation thereof. The results of the determination performed by the controller 11 and/or the apparatus 9 can be displayed on the monitor 15 or plotted by means of a—not displayed but optionally also encompassed—plotter or stored by means of the database 13 or any other storage means. The database 13 can also comprise a computer program initiating the method according to the invention when executed.

In particular, the controller 11 can be configured for carrying out any method according to the invention.

Figure 8:
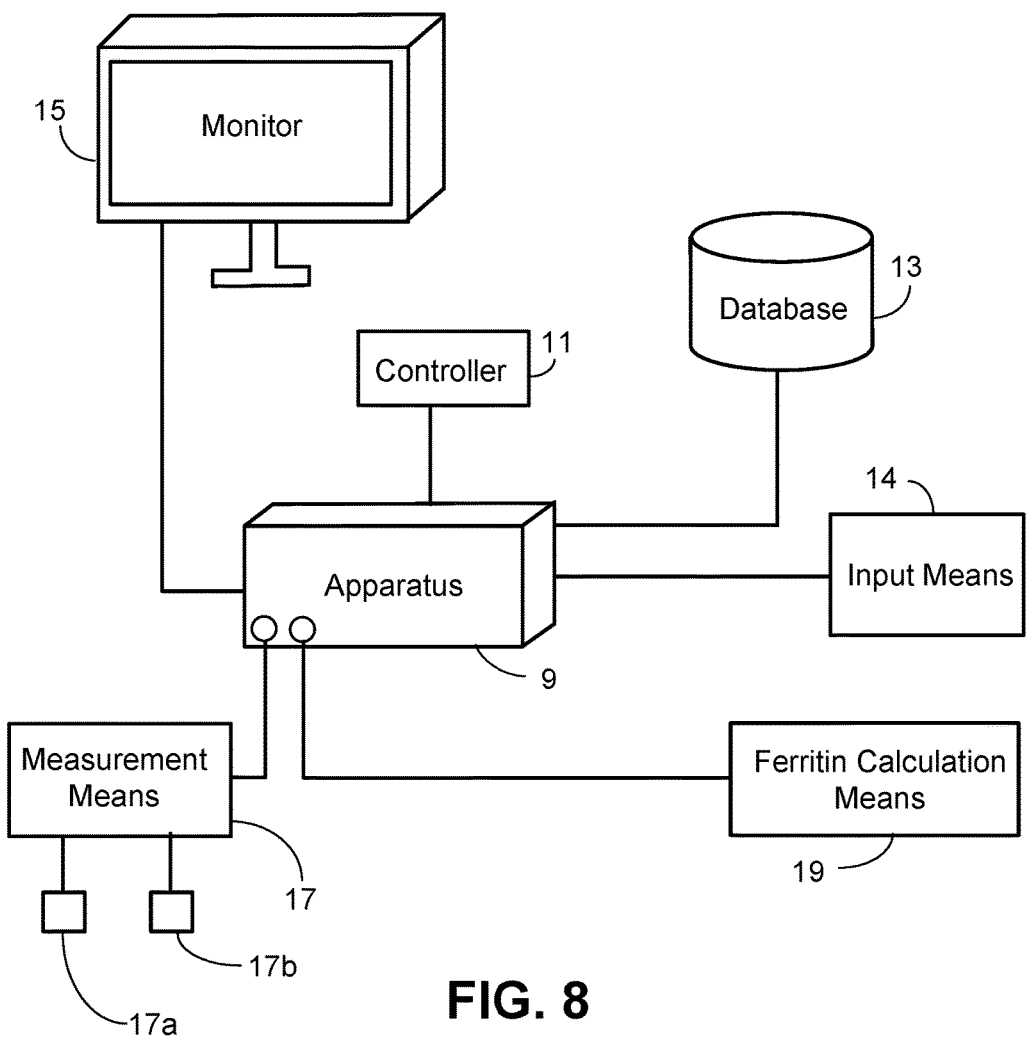
FIG. 8 shows a second apparatus according to the present invention comprising a controller for carrying out the method according to the invention.

As can be seen from FIG. 8, for corresponding measurements the apparatus 9 can be connected (by means of wires or wireless) with a bioimpedance measurement means 17 as one example of a means for measuring or calculating the blood volume. Generally, the means for measuring or calculating the blood volume can be provided in addition to the external database 13 comprising the results of measurements and the data needed for the method according to the invention, or in place of the external database 13 (that is, as an substitute).

The bioimpedance measurement means 17 can be capable of automatically compensating for influences on the impedance data like contact resistances.

An example for such a bioimpedance measurement means 17 is a device from Xitron Technologies, distributed under the trademark Hydra™ that is further described in WO 92/19153, the disclosure of which is hereby explicitly incorporated in the present application by reference.

The bioimpedance measurement means 17 may comprise various electrodes. In FIG. 8, only two electrodes 17a and 17b shown which are attached to the bioimpedance measurement means 17. Additional electrodes are, of course, also contemplated.

Each electrode implied can comprise two or more ("sub"-)electrodes in turn. Electrodes can comprise a current injection ("sub-")electrode and a voltage measurement ("sub-")electrode. That is, the electrodes 17a and 17b shown in FIG. 8 can comprise two injection electrodes and two voltage measurement electrodes (i.e., four electrodes in total).

Similarly, the apparatus 9 may have means 19 for measuring or calculating means for obtaining a value reflecting the mass, the volume or the concentration of ferritin and/or Hb that can again be provided in addition to the external database 13 already comprising the results of measurements and the data needed for the method according to the invention, or in place of the external database 13 (that is, as a substitute).

The means 19 can be provided as a keyboard, touch screen etc. for inputting the required data, sensors, interconnections or communication links with a lab, a ferritin or Hb concentration probe, any other input means, etc.

The apparatuses of FIGS. 7 and 8 may be comprised by a blood treatment apparatus (not shown) according to the present invention or connected therewith.

Again, it is noted that the figures relate examples showing how one embodiment according to the invention may be carried out. They are not to be understood as to limit the invention.

Also, the embodiments according to the invention may comprise one or more features as set forth below which may be combined with any feature disclosed somewhere else in the present specification wherever such combination is technically possible from the perspective of the skilled person.

The invention claimed is:

1. A method for determining or approximating a daily loss of iron (fe_loss) of a patient with impaired renal function, the method comprising the steps:

determining the patient's iron uptake (fe_uptake);

determining a quantity of iron stored within the patient's body by adding at least a value representing a quantity of functional iron stored in the patient's body and a value representing a quantity of non-functional iron stored in the patient's body;

measuring at least one of: a hemoglobin value (Hb), a blood volume, and a concentration of ferritin in serum;

determining the patient's daily loss of iron based on the patient's iron uptake (fe_uptake) and the quantity of non-functional iron stored in the patient's body, using the formula:

$$fe\_loss = fe\_non\text{-}functional\_stored + fe\_Hb - fe\_uptake$$

wherein:

fe_uptake = the patient's iron uptake fe_loss = the patient's daily loss of iron fe_Hb = the quantity of iron stored within the haemoglobin (Hb)

fe_non-functional stored = the quantity of iron stored within the patient's body outside of Hb; and administering a supplemental dosage of iron to the patient during or between dialysis sessions, wherein the supplemental dosage is determined based on the patient's determined daily loss of iron.

2. The method according to claim 1, wherein at least one of:

the functional iron stored in the patient's body is determined using at least one of the haemoglobin value (Hb) and the blood volume; and the quantity of non-functional iron stored within the patient's body is determined using the concentration of ferritin in serum.

3. The method according to claim 1, further comprising at least one of:

determining the patient's iron uptake (fe_uptake) based on cumulating the patient's iron uptake over time; and determining a ferritin curve comprising a series of ferritin measurements over time.

4. A medicament comprising iron for use in the treatment or prevention of anaemia or for enhancing haemoglobin concentration in a patient's blood, wherein the dose of iron to be administered as an iron substitution is set equal to the amount of iron determined to have been lost since the last iron substitution based on the daily loss determined by the method according to claim 1.

5. A non-transitory digital storage means with electrically readable control signals which are able to interact with a programmable computer system such that the method according to claim 1 will be executed.

6. A computer program product having a program code stored on a machine readable data medium for executing the method according to claim 1 when executing the program product on a computer.

7. A computer program having a program code for the execution of the method according to claim 1 when executing the program on a computer.

8. An apparatus for determining or approximating a daily loss of iron of a patient with impaired renal function, the apparatus comprising:

a device configured to input information on the patient's iron uptake (fe_uptake);

a device configured to determine a quantity of iron stored within the patient's body by adding at least a value representing a quantity of functional iron stored within the patient's body and a value representing a quantity of non-functional iron stored within the patient's body;

a device configured to measure at least one of: a haemoglobin value (Hb), a blood volume, and a concentration of ferritin in serum;

a device configured to determine the patient's daily loss of iron based on the patient's iron uptake (fe_uptake) and the quantity of iron stored within the patient's body, wherein the device is configured to determine patient's daily loss of iron using the formula:

$$fe\_loss = fe\_non\text{-}functional\_stored + fe\_Hb - fe\_uptake$$

wherein:

fe_uptake=the patient's iron uptake fe_loss=the patient's loss of iron fe_Hb =the quantity of iron stored within the haemoglobin (Hb)

fe_non-functional_stored=the quantity of iron stored within the patient's body outside of Hb; and a device configured to determine a supplemental dosage of iron to be administered to the patient during or between dialysis sessions, wherein the supplemental dosage is determined based on the patient's determined daily loss of iron.

9. The apparatus according to claim 8, further comprising at least one of:

a device configured to determine the functional iron comprised by the patient by using at least one of the haemoglobin value (Hb) and the blood volume; or a device configured to determine the quantity of non-functional iron stored within the patient's body by using the concentration of ferritin in serum.

10. The apparatus according to claim 8, further comprising:

a device configured to determine the patient's iron uptake (fe_uptake) based on cumulating the patient's iron uptake over time; and a device configured to determine a ferritin curve comprising a series of ferritin measurements over time.

11. A blood treatment apparatus, comprising a device for administering a medicament to a patient, and at least one apparatus according to claim 8, or being in signal communication with the at least one apparatus according to claim 8, wherein the device for administering the medicament is in signal communication with the device configured to determine the daily iron loss.

12. The blood treatment apparatus according to claim 11, configured as a dialysis machine, a hemodiafiltration apparatus, or a hemofiltration apparatus.

* * * * *

UNITED STATES PATENT AND TRADEMARK OFFICE
CERTIFICATE OF CORRECTION

PATENT NO. : 10,406,272 B2
APPLICATION NO. : 15/026319
DATED : September 10, 2019
INVENTOR(S) : Ulrich Moissl et al.

It is certified that error appears in the above-identified patent and that said Letters Patent is hereby corrected as shown below:

On the Title Page

Column 2 item (57) (Abstract), Line 8, delete "erythropoesis" and insert --erythropoiesis--.

In the Claims

Column 12, Line 60, Claim 1, delete "functional stored" and insert --functional_stored--.

Column 14, Line 8, Claim 8, delete "fe _uptake=" and insert --fe_uptake=--.

Column 14, Line 10, Claim 8, delete "fe _Hb" and insert --fe_Hb--.

Signed and Sealed this
Nineteenth Day of November, 2019

Andrei Iancu
*Director of the United States Patent and Trademark Office*